United States Patent [19]
Breed et al.

[11] Patent Number: 5,981,796
[45] Date of Patent: Nov. 9, 1999

[54] PROCESS FOR THE MANUFACTURE OF CARBOXYLIC ACIDS

[75] Inventors: Anthonius Johannes Maria Breed; Rene Johan Haan; Jean-Paul Lange, all of Amsterdam; Leonardus Petrus, Rotterdam, all of Netherlands

[73] Assignee: Shell Oil Company, Houston, Tex.

[21] Appl. No.: 09/030,111

[22] Filed: Feb. 25, 1998

[30] Foreign Application Priority Data

Feb. 25, 1997 [EP] European Pat. Off. ............. 97200537

[51] Int. Cl.$^6$ ............................. C07C 51/14; C07C 51/10
[52] U.S. Cl. ............................................ 562/521; 562/517
[58] Field of Search ................................. 562/521, 517

[56] References Cited

U.S. PATENT DOCUMENTS

| | | |
|---|---|---|
| 5,227,521 | 7/1993 | Richard et al. . |
| 5,250,726 | 10/1993 | Burke . |
| 5,885,488 | 3/1999 | Konijn . |

FOREIGN PATENT DOCUMENTS

| | | |
|---|---|---|
| 249976 | 12/1987 | European Pat. Off. . |
| 92/18592 | 10/1992 | WIPO . |
| 96/20154 | 4/1996 | WIPO . |

*Primary Examiner*—Paul J. Killos
*Assistant Examiner*—J. Parsa

[57] ABSTRACT

A process is provided for manufacture of branched carboxylic acids from branched olefins by means of reaction with carbon monoxide and a solid acid catalyst. In this process, a branched olefin, or a precursor thereof, is reacted in continuously backmixed reactor, with continuously supplied carbon monoxide and water, while continuously an effluent is withdrawn comprising branched carboxylic acid, non-converted olefin, carbon monoxide and water, in the presence of an acidic ion exchanger, having sufficient acid groups to provide requisite protons for conversion of the olefin or a precursor of it, and carbon monoxide into branched carboxylic acids.

15 Claims, No Drawings

PROCESS FOR THE MANUFACTURE OF CARBOXYLIC ACIDS

FIELD OF THE INVENTION

The invention relates to a process for the manufacture of carboxylic acids. More in particular the invention relates to a process for the manufacture of branched carboxylic acids by means of a Koch synthesis using carbon monoxide as reagent and a solid acid catalyst.

BACKGROUND TO THE INVENTION

The up to now available processes are characterized by the fact that no solid acid catalyst could be used, unless the catalyst is operated under unattractively severe conditions or unless the catalyst is combined with corrosive Lewis acid cocatalyst or unless the catalyst is used in a non-aqueous reaction system.

In particular from International Application WO 96/20154 a process is known for production of trialkylacetic acids from branched olefins and carbon monoxide in a non-aqueous reaction system using a solid resin catalyst comprising a cationic resin, having sufficient acid groups to provide requisite protons for conversion of branched olefin and carbon monoxide to trialkylacetic acids.

In particular the cationic resin was specified to have an acidity of at least equivalent to that of a 65 wt % sulphuric acid.

It will be appreciated by an average person skilled in the art that the process can only be performed in two steps, in the first step of which stoichiometric amounts of branched olefin and water will not lead to the desired products in an acceptable yield. Moreover, the process cannot produce more than 1 mole of converted olefin per mole active proton on the solid catalyst in one cycle of two steps.

In WO 92/18592 a process is suggested for manufacture of trialkylacetic acids and particularly of pivalic acid, from branched olefins and particularly isobutene, and carbon monoxide, using a solid acid catalyst together with minor amounts of a Lewis acid, such as boron trifluoride.

EP-A-0249976 suggests a process for the manufacture of branched carboxylic acids, by catalytic conversion of olefins with carbon monoxide and water in the presence of zeoliths as catalysts at temperatures of from 200 to 500° C. and at pressures of 200 to 700 bar.

More in particular zeoliths of the pentasil type are used as catalysts. According to the exemplified embodiments only high temperatures (300° C.) and pressures (300–500 bar) are used.

It will be appreciated that the disclosed reaction conditions will give rise to higher operation costs due to required measures as to safety and environment.

Therefore there is still a strong need for further improvement of the manufacturing process of branched carboxylic acids, starting from branched olefins and carbon monoxide.

An object of the present invention is to provide an improved manufacturing process for branched carboxylic acids, which process uses relatively mild conditions on the one hand and which shows high conversion and high selectivity to branched acids on the other hand.

SUMMARY OF THE INVENTION

This and other objects are accomplished by a process for manufacture of branched carboxylic acids from branched olefins by means of reaction with carbon monoxide and a solid acid catalyst, wherein that a branched olefin, or a precursor thereof, is reacted in a continuously backmixed reactor, and sufficient stirring of the feed components and product occurs to obtain an efficient backmixing with continuously supplied carbon monoxide and water, while continuously an effluent is withdrawn comprising branched carboxylic acid, non-converted olefin, carbon monoxide and water in the presence of an acidic ion exchanger, having sufficient acid groups to provide requisite protons for conversion of the olefin or a precursor of it, and carbon monoxide into branched carboxylic acids.

More in particular the invention relates to an improved manufacturing process of trialkylacetic acids of the formula

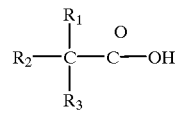

wherein each symbol R represents a radical having 1 to 10 carbon atoms.

More preferably the total number of carbon atoms in the trialkylacetic acids ranges from 5 to 19 and most preferably from 5 to 14, derived from $C_4$-$C_{14}$ olefins.

With the term "branched olefin or a precursor thereof" as used throughout the present specification is meant that branched olefin itself as well as alcohols, esters or ethers, from which the specific olefin can be easily derived, can be used as starting materials for the present manufacturing process, which makes this process much more flexible than conventional prior art processes.

DESCRIPTION OF A PREFERRED EMBODIMENT

In general all olefins containing at least one tertiary carbon atom or precursors therefor, can be converted by the present process.

Suitable examples of the continuously backmixed reactor, referred to hereinbefore, are continuously stirred tank reactors (CTSTR), fluidized bed reactors or recycle reactors.

The hereinbefore mentioned reactor types are known from, for example, Chemical Reaction Engineering second edition, 1962, O Levenspiel.

The continuously stirred tank reactors or the recycle reactors are preferred.

An important advantage of the process of the present invention is that it shows an improved combination of high conversion degree and high selectivity as to the desired branched carboxylic acid, in comparison to these conventional prior art processes, while operated at relatively mild conditions.

The catalyst to be used for the process of the present invention is a solid acidic ion exchanger, showing a sufficient amount of acid active sites per volume unit catalyst and a strong acid activity of each acid site.

The catalyst can be selected from the group consisting of resins, bearing sulphonic, phosphonic or trihalo acetic acid groups.

Preferably sulfonated resins are applied. More preferably sulfonated resins are used, wherein the resins are copolymers of styrene and divinylbenzene, phenol based resins, poly(tetrafluoroethylene) polymers or siloxane polymers.

In the preferred catalysts, bearing active sulfonic acid groups, the resin is treated to give a sulfonic acid cation-exchange resin capable of providing sufficient protons, for example, the resin having per active site an acid strength equivalent to at least 65 wt % sulphuric acid and preferably to at least 70 wt % sulphuric acid.

Catalyst solid resins, comprising sulfonic acid groups and derived from copolymers from styrene, divinylbenzene and phenol or derived from (tetrafluoroethylene)polymers or from siloxane polymers are preferred.

More preferred are catalysts, which are sulfonated copolymers, derived from styrene and divinylbenzene, having a sulfon group density of >2 meq/ml dry resin, and preferably >3 meq/ml dry resin, while the copolymer has a divinylbenzene content in the range of from 4 to 30 wt % and preferably from 8 to 18 wt %.

Specific more preferred examples of commercial effective catalysts are AMBERLYST 36 or 38, NAFION or DELOXAN catalysts (AMBERLYST 36 or 38 or NAFION and DELOXAN are Trade Marks).

Most preferred catalysts are AMBERLYST 36 or 38 or NAFION type catalysts. The reaction temperature in the CSTR is in the range of from 25° C. to 200° C. and preferably from 100° C. to 150° C.

The pressure in the reactor is in the range of from 10 to 200 bar and preferably from 50 to 100 bar.

During the reaction an inert organic solvent can be used, which does not interfere with the desired reaction, preferably a solvent which can easily be separated from the other reaction mixture components and recirculated. As organic solvents can be used apolar as well as polar solvents such as ketones, ethers, substituted aromatics, esters and carboxylic acids.

According to a more preferred embodiment of the present process, the branched acid primarily to be produced, is present as solvent in the reactor, and is regularly discharged from it together with water, CO, non-converted olefin and by-products, to keep the liquid level in the reactor constant.

According to one of the preferred embodiments, the CSTR is filled with solvent and catalyst with a catalyst/solvent wt ratio of in the range of from 0.1 to 0.5 w/w and preferably 0.2–0.3 w/w. The respective reactants are continuously introduced into the reactor and reaction mixture is continuously discharged.

The feed of starting olefin is in the range of from 0.01 to 10 g/g/hr, while the water/olefin molar ratio is in the range of from 0.5 to 2 mole/mole and preferably about 1 and the CO/olefin molar ratio is in the range of from 0.5 to 1000 mole/mole and preferably from 1 to 100.

It will be appreciated that, when using water amounts significantly below the hereinbefore specified amounts, the process becomes unattractive due to too low selectivity and that the selectivity and conversion have surprisingly been improved when using stoichiometric water:olefin=1:1 feed.

The invention is further illustrated by the following examples, however without restricting its scope to these specific embodiments.

Example 1

56 grams of dried AMBERLYST 15 were loaded in a 300 ml CSTR reactor, suspended in 145 ml of n-hexanoic acid (solvent), and activated upon heating up to 155° C. under 10 bar CO with regular purge of the gas cap followed by 1 hour at 155° C. under a 80 bar CO flow of 50 g/h. A feed containing propylene trimer water and CO the molar ratio of water:trimer being 1:1 was then admitted to the reactor with a velocity of 8.5, 1.2 and 50 g/h (WHSV of 0.15, 0.021 and 0.9 g/g/h) under continuous stirring of 1100 rpm, the liquid level of the reactor being kept constant by continuously removing the excess liquid product.

Under these conditions the reaction proceeded with about 75–85% conversion and 93–95% selectivity to the branched carboxylic acid having 10 carbon atoms (VERSATIC acid 10), for some 24 h.

Comparative Example 1

20 grams of AMBERLYST 15 were loaded in a stirred batch reactor, dried for 2 hours at 110° C. under vacuum, suspended in a solution of 50 grams propanoic acid (solvent), 6 grams propylene trimer 3 and 0.8 g water and, finally, heated to 150° C. under 80 bar CO for 65 hours.

Under these conditions the reaction proceeded with about 91% conversion and 8% selectivity to the branched carboxylic acid having 10 carbon atoms (VERSATIC acid 10).

Example 2

In the same way as described in example 1 NAFION NR 50 catalyst (59 grams), dissolved in 120 ml hexanoic acid was used for the conversion of propylene trimer with CO and $H_2O$ into branched carboxylic acids, containing 10 carbon atoms, under the following conditions

| | |
|---|---|
| propylene trimer | 8.8 g/h (WHSV = 0.16 g/g/h) |
| water | 1.2 g/h (WHSV = 0.021 g/g/h) |
| CO | 52 g/h (WHSV = 0.9 g/g/h) |
| temperature | 155° C. |
| pressure | 80 bar |

The conversion was 88 mol % and the selectivity was 91 mol %

Comparative Example 2

13.6 grams of dried AMBERLYST 38 were loaded in a 240 ml stirred autoclave, dried for 2 hours at 150° C. under vacuum, cooled to room temperature, suspended in 74 grams of pivalic acid (solvent), pressurized under 70 bar CO and heated up to reaction temperature of 150° C. During the heating period, 23.4 grams of DIBC (di-isobutyl-carbinol) were slowly and continuously introduced into the autoclave over 17 hours. At the end of the run, the reactor was cooled down and emptied for analysis.

Under these conditions the reaction proceeded with nearly 100% conversion and about 56% selectivity to branched carboxylic acid, having 10 carbon atoms (VERSATIC acid 10).

Comparative Example 3

Example 1 was run with 20.4 grams DIBC being added at once in the stirred reactor (i.e. batch) before pressurizing it to 70 bar CO and raising the temperature to 150° C. The reaction was again carried out for 17 hours.

Under these conditions the reaction proceeded with nearly 100% conversion and about 13% selectivity to branched carboxylic acid, having 10 carbon atoms (VERSATIC acid 10).

Example 3

Example 1 was run using now AMBERLYST 36 as catalyst. The amounts of catalyst, feed and solvent were about 4 times smaller, namely 3.1, 7.4 and 19 grams, respectively.

Under these conditions the reaction proceeded with about 85% conversion and about 32% selectivity to branched carboxylic acid, having 10 carbon atoms (VERSATIC acid 10).

Comparative Example 4

Comparative example 2 was run as batch process with 4 times amounts of catalyst, feed and solvents, namely with 12.1, 20.3, 79 grams, respectively. But the feed was added at once before pressurizing the reactor to 70 bar CO and raising the temperature to 150° C.

Under these conditions the reaction proceeded with about 93% conversion and about 2.7% selectivity to branched carboxylic acid, having 10 carbon atoms (VERSATIC acid 10).

We claim:

1. A process for manufacture of branched carboxylic acids from branched olefins by means of reaction with carbon monoxide and a solid acid catalyst, characterized in that a branched olefin, or a precursor thereof is reacted in continuous backmixed reactor, wherein sufficient stirring of the feed components and product occurs to obtain an efficient backmixing with continuously supplied carbon monoxide and water, while continuously an effluent is withdrawn comprising branched carboxylic acid, non-converted olefin, carbon monoxide and water, in the presence of an acidic ion exchanger, having sufficient acid groups to provide requisite protons for conversion of the olefin or a precursor of it, and carbon monoxide into branched carboxylic acids.

2. The process of claim 1, wherein the trialkylacetic acids of the formula

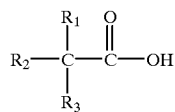

are produced, wherein each symbol R represents a radical having 1 to 10 carbon atoms.

3. The process of claim 1 wherein the total number of carbon atoms in the trialkyl acetic acids is in the range of 5 to 19.

4. The process of claim 3 wherein the total number of carbon atoms in the trialkylacetic acids is in the range of 5 to 14.

5. The process of claim 1 wherein the solid acid catalyst is a solid acidic ion exchanger the ion exchanger selected from the group consisting of sulfonated resins, sulfonated poly(tetrafluoro-ethylene) and sulfonated siloxane polymers.

6. The process of claim 1 wherein the solid catalyst is an acidic ion exchanger is a sulfonated copolymer of styrene and divinylbenzene or phenolic base resins.

7. The process of claim 5 further comprising the step of treating the resin to give a sulfonic acid cation-exchange resin, such that the resin having per active site an acid strength equivalent to at least 65 wt % sulphuric acid and preferably to at least 70 wt % sulphuric acid.

8. The process of claim 1 wherein the solid catalyst is a sulfonated copolymer derived from styrene and divinylbenzene, having a sulfon group density of greater than 2 meq/ml dry resin while the copolymer has a content of divinylbenzene in the range of 4 to 30 wt %.

9. The process of claim 8 wherein the solid catalyst has a sulfon group density of greater than 3 meq/ml dry resin.

10. The process of claim 8 wherein as catalyst has a content of divinylbenzene in the range of 8 to 18 wt %.

11. The process of claim 1 wherein the pressure in the reactor is in the range of from 50 to 100 bar.

12. The process of claim 1 wherein during the reaction a branched acid primarily to be produced, is present as solvent in the reactor.

13. The process of claim 1 wherein the continuous backmixed reactor is operated at a temperature in the range of 25° C. to 200° C.

14. The process of claim 1 wherein the continuous backmixed reactor is operated at a pressure in the range of 10 to 200 bar.

15. The process of claim 14 wherein the continuous backmixed reactor is operated at a temperature in the range of 25° C. to 200° C.

* * * * *